United States Patent [19]

Eneroth et al.

[11] 4,198,567
[45] Apr. 15, 1980

[54] METHOD AND APPARATUS FOR DISCRIMINATION BETWEEN SCATTERED EXCITATION RADIATION AND LOW LEVEL FAST DECAYING FLUORESCENT RADIATION

[76] Inventors: Peter Eneroth, Framnäsbacken 22, S-171 42 Solna; Wladimir Wladimiroff, St. Olofsgatan 43B, S-753 30 Uppsala, both of Sweden

[21] Appl. No.: 845,195

[22] Filed: Oct. 25, 1977

[51] Int. Cl.² .................... G01T 1/10; G01N 21/38
[52] U.S. Cl. ............................. 250/459; 250/461 R
[58] Field of Search .............. 250/458, 459, 461 R, 250/461 B; 356/85, 96, 97, 98

[56] References Cited
U.S. PATENT DOCUMENTS

| | | | |
|---|---|---|---|
| 4,006,360 | 2/1977 | Mueller | 250/461 B |
| 4,037,961 | 7/1977 | Macemon | 250/461 R |
| 4,055,768 | 10/1977 | Bromberg | 250/461 R |
| 4,058,732 | 11/1977 | Wieder | 250/461 B |

*Primary Examiner*—Davis L. Willis
*Attorney, Agent, or Firm*—Pollock, Vande Sande & Priddy

[57] ABSTRACT

A gated, pulsed laser spectrofluorometer is provided analyzing subpicogram amounts of fluorescent substance in sample volumes of less than 10 μl. This is accomplished by repetitively exciting the fluorescent sample with a subnanosecond, intensive excitation radiation pulse and by gating a fluorescence radiation detector output signal so that detection starts after the excitation radiation pulse has decayed to a negligible intensity and ends when the fluorescence radiation detector output signal caused by the fluorescence emission from the sample has decayed to a level comparable to the electrical noise level of the electronic measuring apparatus connected to said fluorescence radiation detector.

19 Claims, 7 Drawing Figures

METHOD AND APPARATUS FOR DISCRIMINATION BETWEEN SCATTERED EXCITATION RADIATION AND LOW LEVEL FAST DECAYING FLUORESCENT RADIATION

BACKGROUND OF THE INVENTION

The wavelength position and structure of the fluorescence emission spectrum of a fluorescent sample in the gaseous phase or in liquid respectively solid solution is typical of the chemical composition of the sample and is also typical of the sample phase. Fluorescence emission has a nanosecond duration and upon excitation of the fluorescence of a sample by a subnanosecond radiation pulse the fluorescence emission intensity decay curve can be recorded as a function of time. This decay curve is again typical of the chemical composition and the phase of the sample.

The fluorescence emission intensity originating from a fluorescent substance is linearly proportional to the concentration of the substance and in known apparatus the fluorescence emission intensity is measured in order to determine the fluorescent substance concentration in the sample. Often, in cases where the nature of an unknown substance has to be determined, the fluorrescence wavelength spectrum is recorded. As shown in FIG. 6, such measurements usually are carried out by illuminating the sample with light from a continuous light source, such as a high-pressure xenon arc, or a pulsed light source, such as a flash lamp, the excitation radiation being passed through a monochromator (A) selecting the excitation wavelength prior to falling into the sample and the resulting fluorescence emission being passed through a monochromator (B) prior to falling onto a fluorescence radiation detector. The wavelength settings of the two monochromators are ideally such that the light passing through monochromator (A) cannot pass through monochromator (B), in this way avoiding that the radiation detector measuring the fluorescence emission intensity will also be irradiated with light originating from the excitation light source.

However, even the best monochromators have a finite transmission for other wavelengths but the central setting wavelength in the form of stray light and the sensitivity of known fluorescence spectrophotometric apparatus is primarily limited by the circumstance that all fluorescent samples, apart from absorbing the excitation radiation causing the sample fluorescence, will scatter part of the excitation radiation and as monochromator (B) will transmit part of this scattered excitation radiation independently of its central wavelength setting, scattered radiation will be able to reach the fluorescence radiation detector. When the concentration of the fluorescent substance in the sample is so low that its fluorescence intensity is less than the intensity of the scattered excitation radiation reaching the detector, the fluorescence emission cannot be detected in known apparatus.

The light scattering ability of molecules increases with increasing molecular size and consequently the study of the fluorescence emission from biological systems, such as proteines and living tissues, is seriously hampered by light scattering. However, fluorescence studies of such systems are of central importance in the elucidation of biochemical aspects of human diseases and the object of the present invention is to provide a method and apparatus which overcome the sensitivity limitations of known fluorescence spectrophotometers and thus provide a means of analysing hitherto undetectable low levels of fluorescence intensity.

SUMMARY OF THE INVENTION

The present invention provides a method and apparatus for the analysis of small amounts of fluorescent substance by measuring the fluorescence emission intensity and wavelength spectrum. The signal induced into a fast fluorescence radiation detector by the scattered radiation from a subnanosecond excitation pulse is allowed to decay until it has reached a level such that the signal caused by the fluorescence emission from a fluorescent sample excited by said excitation pulse is distinctly larger than the scattered radiation signal. Then the actual detection process is made to start by gating the fluorescence radiation detector signal current to flow into a signal storage capacitor from the moment the scattered radiation signal is negligible until the moment when the fluorescence intensity has decayed to a level causing a fluorescence radiation detector signal comparable to the electrical noise level of the detection electronics. This signal gating sequence is started by an electrical trigger pulse originating from a reference radiation detector which receives a fraction of each excitation radiation pulse reflected from a beam-splitter which is positioned at such a distance from the excitation radiation source that said fraction arrives at the reference radiation detector substantially before the excitation radiation pulse hits the sample. The reference radiation detector is simultaneously used to monitor the excitation radiation pulse intensity. This is accomplished by gating the reference radiation detector signal current to flow into a reference storage capacitor during a time period of the same duration as the duration of the excitation radiation pulse. Thus a sample signal and a reference signal are made available which after division give the relative fluorescence intensity of the sample. By maintaining an excitation radiation pulse repetition rate of up to 100 Hz an apparatus according to the principles of the present invention can analyse subpicogram amounts of fluorescent substance in microliter sample volumes.

DESCRIPTION OF THE PREFERRED EMBODIMENT

Figure 1:
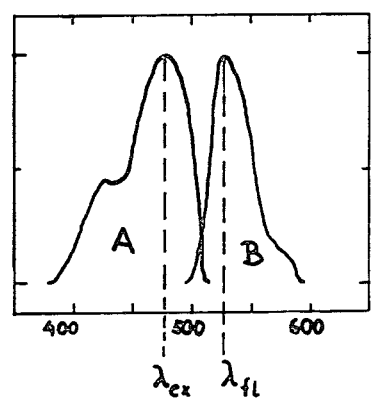
FIG. 1 shows the spectral wavelength distribution of the absorption (A) and of the fluorescence emission (B) of a typical fluorescent compound F.
Figure 2:
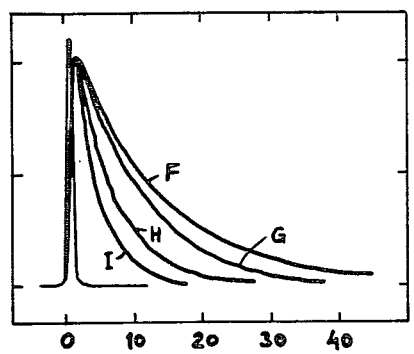
FIG. 2 shows the fluorescence intensity decay curves as a function of time for some typical fluorescent compounds F, G, H, and I, excited with radiation pulses having a decay time of 0.3 ns.

We consider a fluorescent sample F with a radiation absorption spectrum in wavelength region A and a fluorescence emission spectrum in wavelength region B, an illustrated in FIG. 1. Exciting the sample with a radiation pulse of central wavelength $\lambda_{ex}$ and with a decay time much shorter than the fluorescence decay time of the sample, the decay curve of the fluorescence emission intensity at a central wavelength $\lambda_{fl}$ can be recorded. FIG. 2 gives some typical fluorescence decay curves of different samples as recorded in our laboratory with a nitrogen laser—dye laser combination generating excitation pulses with a decay time of 0.3 ns.

The excitation radiation scattered by the sample has a decay time which is identical and isochronous with the excitation radiation pulse decay. It therefore follows (compare FIG. 3) that when detection of the fluorescence emission at e.g. $\lambda_{fl}$ from the sample F is started at a time $t_1$, when the excitation radiation pulse intensity has decayed to a level much lower than the fluorescence emission intensity, only a minute fraction of the scattered radiation of wavelength $\lambda_{ex}$ still can be seen by the fluorescence radiation detector and that as time proceeds this fraction rapidly becomes negligible. At time $t_2$ the fluorescence emission intensity at $\lambda_{fl}$ has decayed to a level causing a fluorescence radiation detector signal level comparable to the electrical noise level of the detection electronics, and at that instant the detection is ceased.

Gating the fluorescence emission intensity detection in this manner has two advantages: firstly, scattered excitation radiation is not interfering with the measurement of the fluorescence emission intensity and secondly, only a minimum of electrical noise is incorporated in the measurement.

Figure 5:
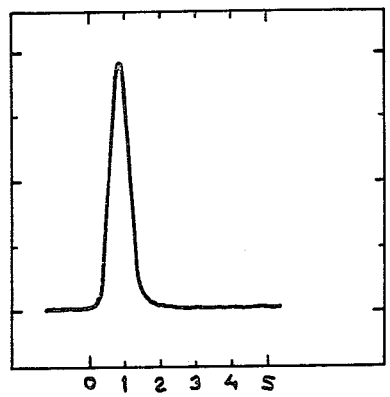
FIG. 5 illustrates the time evolution of a typical laser radiation pulse used to excite the fluorescence emission of samples according to the method of the present invention.
Figure 4:
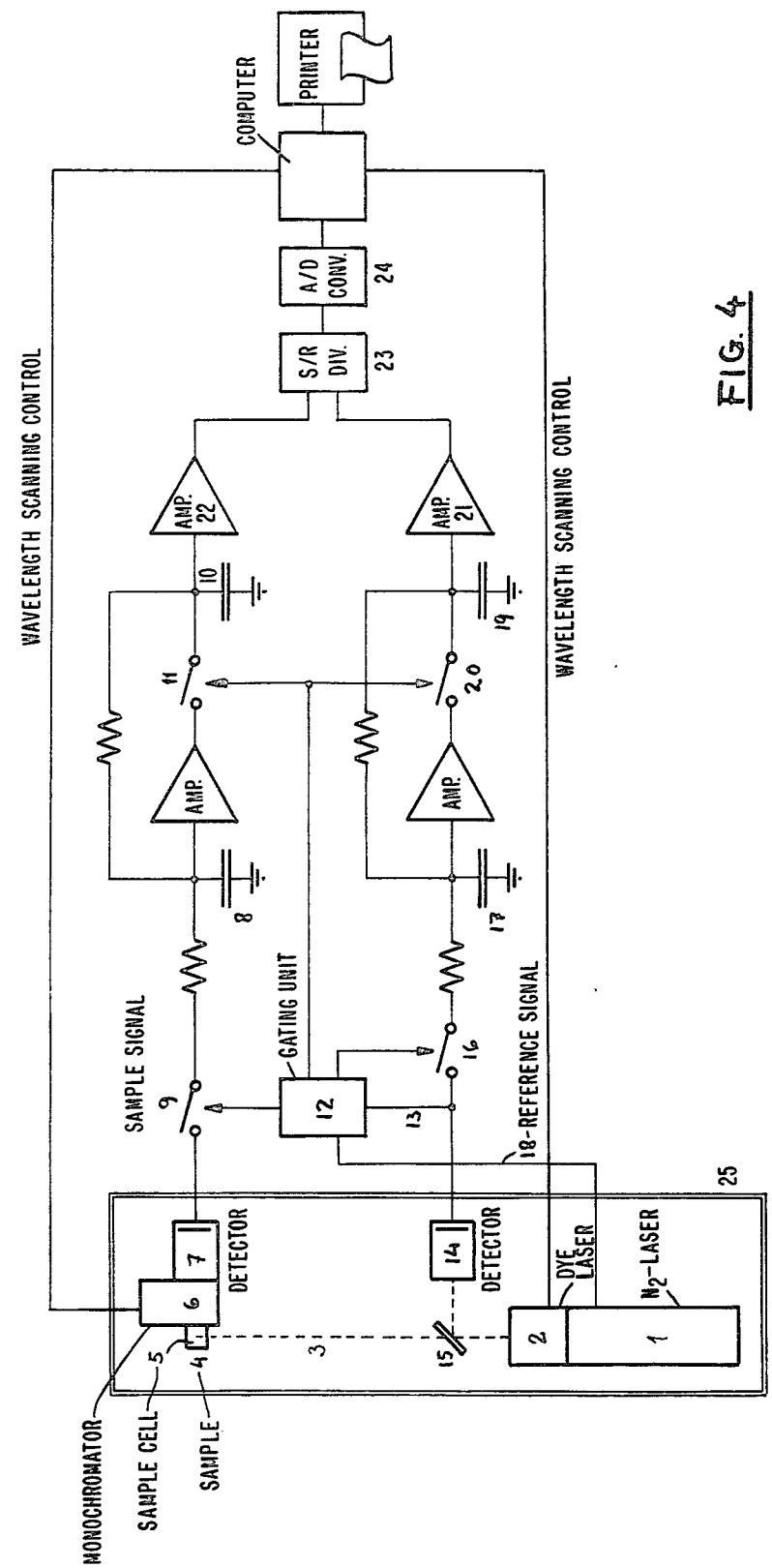
FIG. 4 is a functional description of the principles of a measuring system according to the invention.
Figure 6:
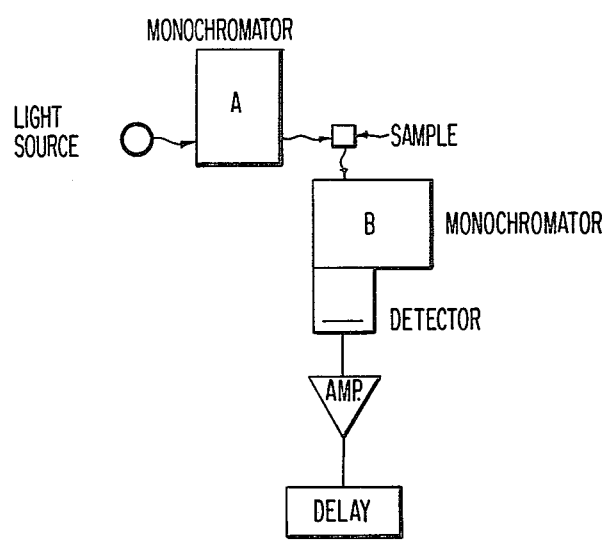
FIG. 6 shows a block diagram of a prior art fluorescence emission measuring device.

An example of an apparatus to measure sample fluorescence according to the described method is arranged as illustrated in FIG. 4. The pulsed laser radiation source exciting the sample 4 preferably consists of a radio-frequency interference-free nitrogen laser 1—dye laser 2 combination from which radiation pulses 3 with a peak power of at least 1 kW and a decay time of 0.5 ns or less are obtained in a wavelength region of variable width and wavelength position. FIG. 5 illustrates the shape of typical laser radiation pulses from such a combination 1–2. Other pulsed laser systems from which equivalent excitation radiation pulses can be obtained may be applied, but the condition of radio-frequency interferencefree operation must be fulfilled in such other systems, as the detection electronics must not be disturbed by external noise. The repetition rate of the excitation radiation pulses is typically in the range 20–100 Hz but can be made higher. The wavelength tunability is typically over at least the spectral region 350–700 nm, while the spectral width of the excitation radiation pulses, measured as full width at half maximum, is variable from at least 1–20 nm. The radiation pulses excite the sample 4 contained in the sample cell 5. The fluorescence emission from the sample passes through monochromator 6, which corresponds to the earlier mentioned monochromator (B). The monochromator (A) mentioned earlier is not needed in an apparatus according to the present invention, as the laser radiation source can be made to emit radiation of continuously variable wavelength.

Monochromator 6 is either set at a fixed wavelength, such as $\lambda_{fl}$, or is made to scan through the fluorescence emission spectrum of the sample. Thus the apparatus is capable of firstly, recording the fluorescence excitation spectrum of the sample, keeping monochromator 6 at a fixed wavelength and having the laser excitation radiation wavelength scan through the absorption spectrum of the sample, secondly, recording the fluorescence emission spectrum of the sample keeping the laser excitation radiation wavelength fixed at e.g. $\lambda_{ex}$ and having monochromator 6 scan through the fluorescence emission spectrum of the sample, and thirdly, only determining the concentration of the sample by measuring the fluorescence emission intensity, keeping both $\lambda_{ex}$ and $\lambda_{fl}$ fixed.

Figure 3A:
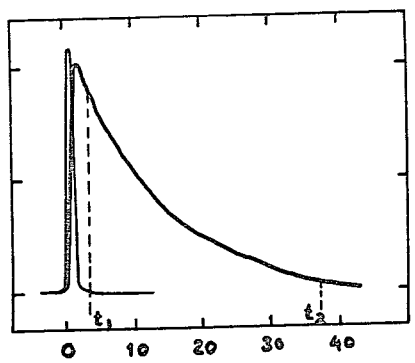
FIGS. 3a and 3b give the start $t_1$ and the end $t_2$ of the gating sequence for the fluorescence radiation detector signal relative to the time of occurrence of the excitation radiation pulse. In 3a the fluorescence emission peak intensity is of the same order of magnitude as the scattered excitation radiation pulse peak intensity. In 3b the fluorescence emission peak intensity is considerably smaller than the scattered excitation radiation pulse peak intensity.
Figure 3B:
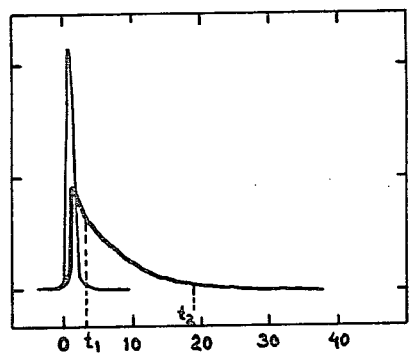

Having passed through monochromator 6 the fluorescence radiation falls onto the fast fluorescence radiation detector 7 which has a rise time of the order of the excitation radiation pulse decay time. The signal coming from the fluorescence radiation detector 7, each time an excitation radiation pulse has hit the sample, is fed into the small signal storage capacitor 8 via the fast switch 9 which is closed and opened by gating unit 12 at times $t_1$ and $t_2$ respectively, as illustrated in FIG. 3. The voltage built up over signal storage capacitor 8 is transferred to the larger signal hold capacitor 10 via switch 11 which is also closed and opened by gating unit 12. The gating unit receives an electrical trigger pulse 13, starting the gating sequence for switch 9, from a fast reference radiation detector 14 which is irradiated by some fraction of the excitation radiation pulse being reflected from beam-splitter 15. The beamsplitter is positioned so that said fraction is made to arrive at the reference radiation detector 14 before the actual excitation radiation pulse 3 arrives at the sample, thus introducing a time difference needed to activate in gating unit 12 the appropriate gating sequence for switch 9.

As the intensity of the excitation radiation pulses coming from the laser radiation source is a function of wavelength and as the excitation radiation wavelength must be changeable in order to be able to excite the maximum fluorescence emission intensity of different samples, the intensity of the excitation radiation pulses is monitored with a fast reference radiation detector 14 by closing and opening switch 16 and charging the reference storage capacitor 17. The electrical trigger signal 18 for the gating sequence of switch 16 comes from the laser radiation source 1 and is routed to gating unit 12 prior to the appearance of the excitation radiation pulse 3. The voltage built up over reference storage capacitor 17 is transfered to the larger reference hold capacitor 19 via switch 20. Both switches 11 and 20 are actuated simultaneously by gating unit 12 once the voltage build-up over storage capacitors 8 and 17 is complete.

The signal from amplifier 22, representing the fluorescence intensity of the sample and the signal from amplifier 21, representing the excitation radiation pulse intensity, are fed into a divider unit 23, the output of which is a signal representing the relative fluorescence intensity from the sample. This signal is independent of the intensity of the excitation radiation pulses. From the divider unit 23 the signal is fed into an analog/digital convertor 24 from which the result of a measurement is available in digital form for further computation, presentation and appropriate administrative handling and storage by a computer unit.

The wavelength positioning mechanisms in both the laser radiation source and in the monochromator 6 can be driven by a stepper motor so that the wavelength setting and control of both $\lambda_{ex}$ and $\lambda_{fl}$ can be taken care of by the computer unit.

The laser combination 1-2, the sample holder 4, the monochromator 6 and both radiation detectors 7 and 14 are contained in a light-tight casing 25 to exclude foreign light from the measurement and to facilitate operation of the apparatus under normal laboratory conditions.

What is claimed is:

1. An apparatus for exciting a fluorescent substance in a gaseous, light or solid state and analyzing predetermined parts of the fluorescence emission decay of the substance, comprising:
   radiation means for generating excitation radiation pulses;
   drive means for generating a pretrigger signal prior to the generation of each excitation radiation pulse;
   fractional deflection means for deflecting a portion of the radiation of each of said excitation radiation pulses and passing the remaining portion of the radiation of said excitation pulses to irradiate said fluorescent substance;
   reference radiation detection means for receiving said deflected portion of radiation and generating a corresponding electrical trigger signal proportional to the intensity of said deflected portion of radiation;
   filter means for receiving the fluorescence emission radiation of said fluorescent substance and passing filtered fluorescence radiation having particular emission wavelengths;
   fluorescence radiation detector means for receiving said filtered fluorescence radiation and generating a corresponding fluorescence electrical signal proportional to the intensity of the filtered fluorescence radiation;
   reference storage means responsive to a reference gating signal to store said trigger signal;
   fluorescence storage means responsive to a sample gating signal to store said fluorescence signal; and
   gating means responsive to said pretrigger signal to generate said reference gating signal and responsive to said trigger signal to generate said sample gating signal at a time after said excitation pulse has reached said fluorescent substance and the corresponding scattered radiation from said excitation pulse has diminished to a level of intensity that is less than the intensity of said fluorescence emission radiation.

2. The apparatus of claim 1 including means for receiving a stored trigger signal and a corresponding stored fluorescence signal and generating a signal corresponding to the ratio of the stored fluorescence signal and the stored trigger signal.

3. The apparatus of claim 1 including means for maintaining said sample gating signal to store said fluorescence signal for as long as the level of intensity of said fluorescence emission radiation is greater than the level of intensity of associated electrical noise.

4. The apparatus of claim 1 wherein said fractional deflection means includes a beam splitter adjustably positioned with respect to said fluorescent substance to define an optical delay substantially equal to the activation time of said gating means minus a time corresponding to the pulse width of an excitation radiation pulse.

5. Apparatus as claimed in claim 1 wherein said radiation means is a nitrogen laser - dye laser combination generating laser radiation pulses with a decay time of less than 1 ns.

6. Apparatus as claimed in claim 5 in which the laser radiation pulses have a continuously variable spectral wavelength in the region 350-700 nm.

7. Apparatus as claimed in claim 6 wherein said laser includes a spectral wavelength variation mechanism that is driven by a stepper motor.

8. Apparatus as claimed in claim 5 in which the laser radiation pulses have a continuously variable spectral width between 1-20 nm.

9. Apparatus as claimed in claim 1 wherein said filter means is a monochromator having an arrangement of fixed central wavelength interference transmission filters.

10. Apparatus as claimed in claim 9 in which the monochromator transmission wavelength is continuously variable over the spectral region between 350-1000 nm.

11. Apparatus as claimed in claim 10 wherein the monochromator includes a wavelength variable mechanism that is driven by a stepper motor.

12. Apparatus as claimed in claim 1 in which the fluorescence radiation detector means includes a fast photomultiplier having a rise time of the order of the fall time of the excitation radiation pulses.

13. Apparatus as claimed in claim 2 in which the reference radiation detection means includes a fast vacuum photodiode having a rise time of the order of the fall time of the excitation radiation pulses.

14. Apparatus as claimed in claim 1 including means for generating an analog signal proportional to the ratio of the stored fluorescence signal and the stored trigger signal.

15. Apparatus as claimed in claim 14 including means for converting said analog signal into a digital signal.

16. Apparatus as claimed in claim 1 including a light-tight casing for holding the radiation means, the filter means, the fluorescence radiation detector means, the fractional deflection means and the reference radiation detection means and excluding ambient light from disturbing the measurements as well as preventing the excitation radiation from irradiating surfaces having no relation to the purpose of the measurements.

17. Method for quantitative analysis of a fluorescent substance with a fast fluorescence decay in a gaseous, liquid or solid state sample, wherein a sample is excited by excitation radiation pulses and certain predetermined parts of the fluorescence emission decay are selected for analysis by means of a fluorescence radiation detector and an associated electronic gating unit, said method comprising the steps of:
   generating excitation radiation pulses;
   irradiating a reference radiation detector by a fraction of each of said excitation radiation pulses, said reference radiation detector generating a trigger pulse directly to said electronic gating unit without introducing any other electronic delay but the inherent transit time of the reference radiation detector;
   delaying the arrival of each of said excitation radiation pulses at said sample by a delay time that is substantially equal to the activation time of said electronic gating unit minus the time-width of an excitation pulse;

exciting the sample fluorescence by means of said delayed excitation radiation pulses;

detecting the fluorescence emission from the sample by means of said fluorescence radiation detector; and applying said trigger pulse to gate the signal from said fluorescence detector to a signal storage means.

18. The method of claim 17 including generating said excitation radiation pulses by a coaxial nitrogen laser in combination with a dye laser, the excitation pulses each having a fall time of less than 1 nanosecond.

19. The method of claim 17 wherein said irradiation step includes splitting each radiation pulse with a beam splitter positioned a variable distance from the sample to generate said fraction of excitation radiation.

* * * * *